United States Patent [19]
Peifer et al.

[11] Patent Number: 5,735,861
[45] Date of Patent: Apr. 7, 1998

[54] CHANNEL MOUNTED ACTIVATING MECHANISM FOR AN ENDOSCOPIC LIGATOR

[75] Inventors: Rodney Peifer, Kernersville; Michael K. Simmons, Winston-Salem, both of N.C.

[73] Assignee: Wilson-Cook Medical, Inc., Winston-Salem, N.C.

[21] Appl. No.: 524,069

[22] Filed: Sep. 6, 1995

[51] Int. Cl.$^6$ .................................................. A61B 17/00
[52] U.S. Cl. ........................................... 606/139; 606/140
[58] Field of Search .................................... 606/139–141

[56] References Cited

U.S. PATENT DOCUMENTS

| | | | |
|---|---|---|---|
| 5,163,948 | 11/1992 | Kummer | 606/152 |
| 5,174,276 | 12/1992 | Crockard | 606/142 |
| 5,197,649 | 3/1993 | Bessler et al. | 227/179 |
| 5,462,559 | 10/1995 | Ahmed | 606/140 |

Primary Examiner—Michael Buiz
Assistant Examiner—T. D. Pham
Attorney, Agent, or Firm—Woodard, Emhardt, Naughton, Moriarty & McNett

[57] ABSTRACT

An activating mechanism for activating an endoscopic ligator is disclosed. The activating mechanism includes a mounting component and an activating component coupled thereto. The mounting component inserts directly into the operating channel of an endoscope and is dimensioned to maintain a friction fit within the operating channel to mount the mechanism to the endoscope. The mounting component includes a channel for receiving an activation line of the ligating device which is threaded through the operating channel and the channel in the mounting component, and onto the activating component of the activating mechanism. The activation line attaches to a spool of the activating component. The activating component further provides a drive pin and a roller clutch for setting the activating component in an engaged or a disengaged position and a knob for rotating the drive pin. When the drive pin is engaged with the roller clutch, the knob can only rotate in one direction. When the drive pin is in the disengaged position from the roller clutch, the knob can rotate in either direction.

13 Claims, 14 Drawing Sheets

CHANNEL MOUNTED ACTIVATING MECHANISM FOR AN ENDOSCOPIC LIGATOR

BACKGROUND OF THE INVENTION

1. Field of the Invention

The invention relates to the field of endoscopic ligation. More particularly, the invention relates to devices which are used to activate an endoscopic ligator for ligating lesions within a hollow organ of the body.

2. Background

Endoscopic ligating devices which apply elastic rings over selected body tissue are well known in the prior art. The ligating device is typically activated by retracting a line (string, wire, or cable) that is attached to the ligator at the distal end of an endoscope and is threaded through the operating channel of the endoscope to the proximal end of the instrument. The ligator can be activated by manually pulling on the activating line. Mechanically assisted operation has also been provided by means of a hand operated reel or trigger, or a motor drive mechanism.

SUMMARY OF THE INVENTION

The present invention provides a new and unique activating mechanism for an endoscopic ligator which securely mounts to an endoscope and operates to provide precise control to effectuate ligation. The device is easy and convenient to use, and can be simply disconnected widen the ligation procedure has been completed.

As shown in the following description of the preferred embodiment, an activating mechanism mounts to an endoscope by means of a mounting component which is inserted directly into the operating channel of the endoscope and is friction fitted therein. In this way, the activating mechanism securely mounts to the endoscope with a single motion. The attachment is securely sealed during the procedure, and can be easily disconnected after the ligation has been performed. There is further provided means for activating the ligating device which is precisely controllable and which can be simply disconnected upon the completion of the ligation procedure. As shown, an activating component operates in a working mode in which the activation line can be retracted under precisely controlled tension to release the ligating bands as desired. When the procedure is suspended or completed, the activating component cart be switched to a disengaged mode in which tension on the activation line is released to prevent unintended band release and to allow for easy disconnection of the activation line from the activating component.

It is an object of the present invention to provide an activating mechanism for an endoscopic ligator which easily mounts to the endoscope in a stable fashion.

It is a further object of the present invention to provide an activating mechanism for an endoscope which mounts to the endoscope by securely attaching into the operating channel of the endoscope.

It is a further object of the present invention to provide an activating mechanism for an endoscopic ligator which is precisely controllable to effectuate endoscopic ligation as desired.

It is a further object to provide such an activating mechanism which is convenient to use and which can be readily disconnected at the completion of the procedure.

These and other objects and advantages of the present invention will be apparent from a review of the following description of the preferred embodiment.

DETAILED DESCRIPTION OF THE PREFERRED EMBODIMENT

For the purposes of promoting an understanding of the principles of the invention, reference will now be made to the embodiment illustrated in the drawing and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
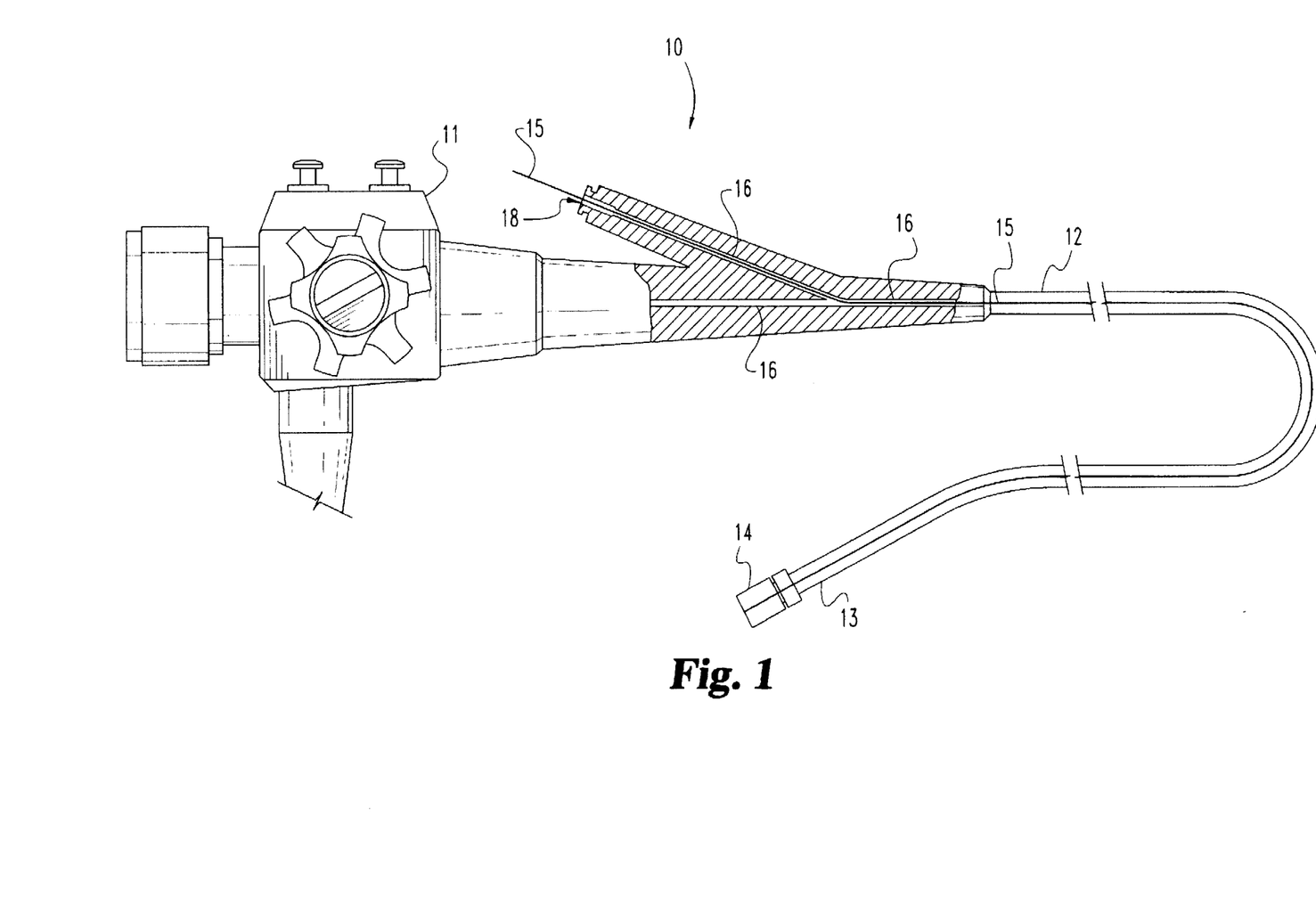
FIG. 1 is a longitudinal fragmented view of an endoscope with an endoscopic ligator (generally shown) that is located at the distal end of the endoscope.

Referring more particularly to the drawings, there is shown in FIG. 1 endoscope 10 with endoscopic ligator 14 attached to the distal end of endoscope 10. Endoscopic ligator 14 is generally shown in FIG. 1. A more detailed description of ligator 14 is shown in pending U.S. application Ser. No. 08/260,380 filed on Jun. 14, 1994, and specifically FIGS. 16-20 therein and descriptions thereof, which disclosure is hereby incorporated by reference. Endoscope 10 is a conventional endoscope with an operating control portion 11, a flexible section 12, and a distal end portion 13. Endoscopic ligator 14 is located at distal end portion 13 of endoscope 10 and includes an activation line 15. Endoscope 10 also includes operating channel 16 which extends through endoscope 10 from distal end portion 14 to operating control portion 11 and to proximal opening 18. Activation line 15 is threaded from ligator 13 through operating channel 16 and exits through proximal opening 18.

Figure 2:
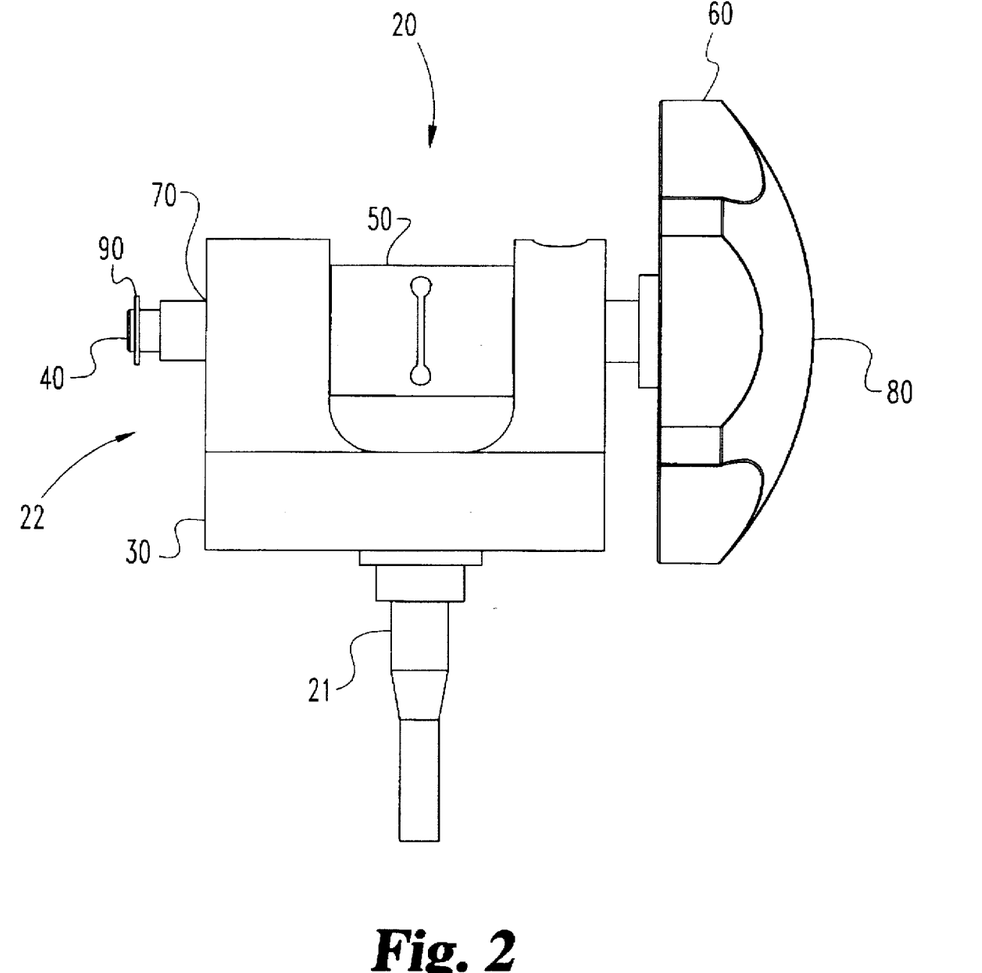
FIG. 2 is a top plan view of an activating mechanism for activating the endoscopic ligator of FIG. 1.

FIG. 2 is a top plan view of an activating mechanism 20 according to the present invention. Activating mechanism 20 includes mounting component 21 and activating component 22. Activating component 22 includes base 30, drive pin 40, spool 50, knob 60, roller clutch 70, bolt 80 and retaining clip 90. Mounting component 21 attaches to activating component 22 and is used to mount activating mechanism 20 to endoscope 10 at opening 18.

Figure 3A:
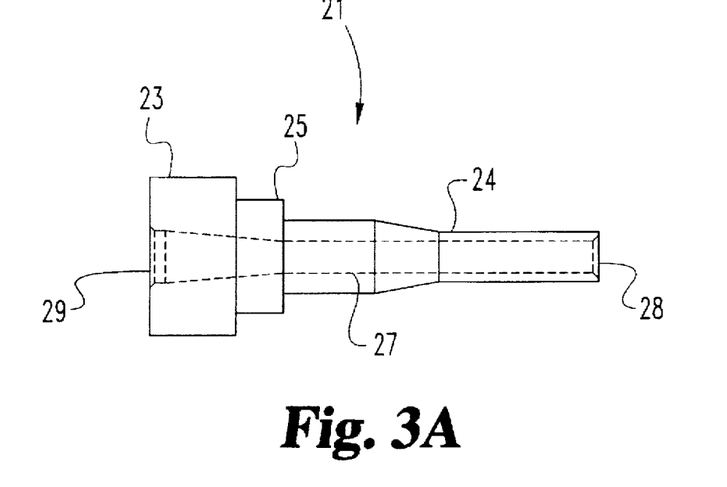
FIGS. 3A-3C are views of a mounting component of the activating mechanism of FIG. 2.
Figure 10:
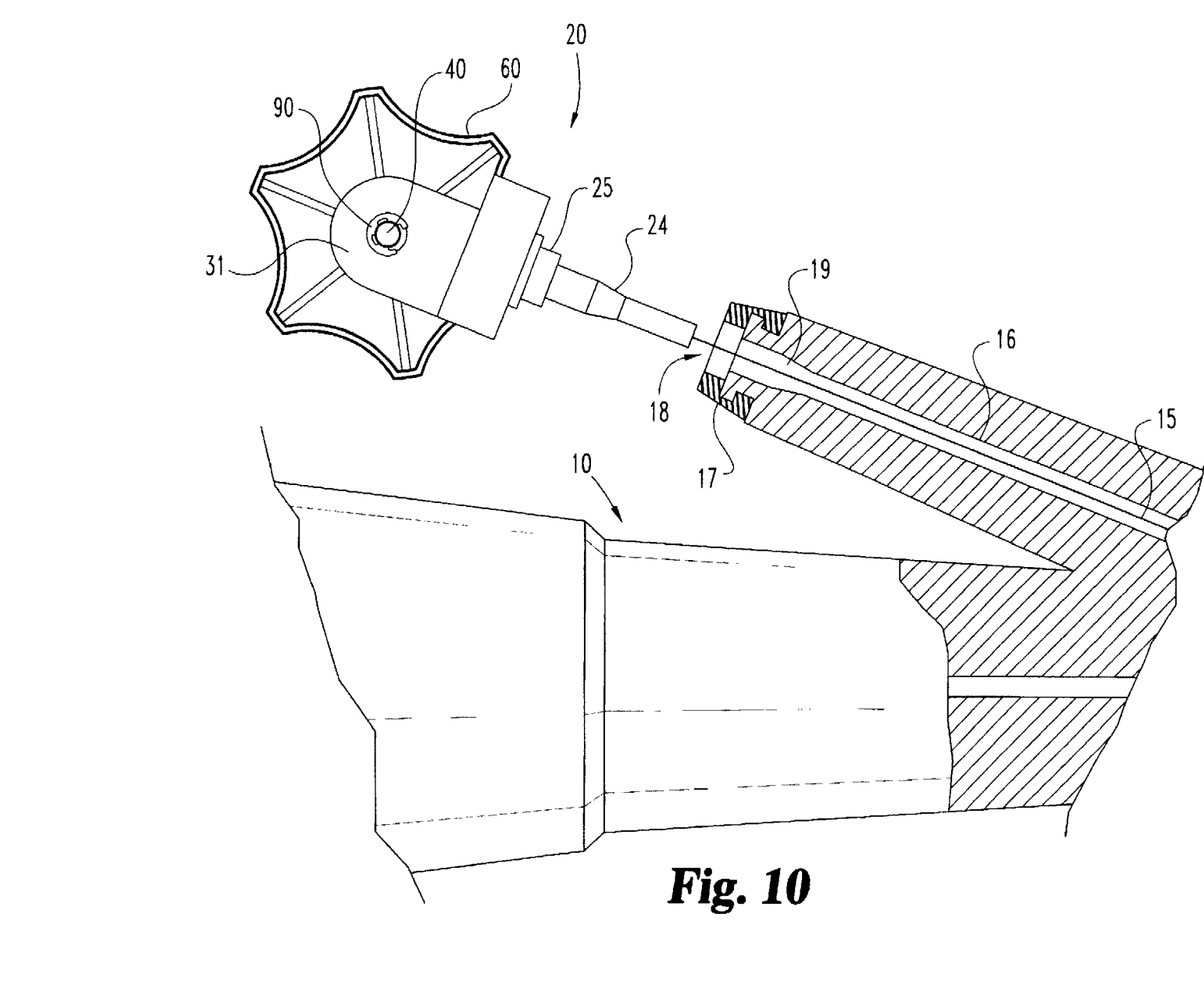
FIG. 10 is a view of the activating mechanism of FIG. 2 prior to insertion into the operating channel of the endoscope of FIG. 1.
Figure 11:
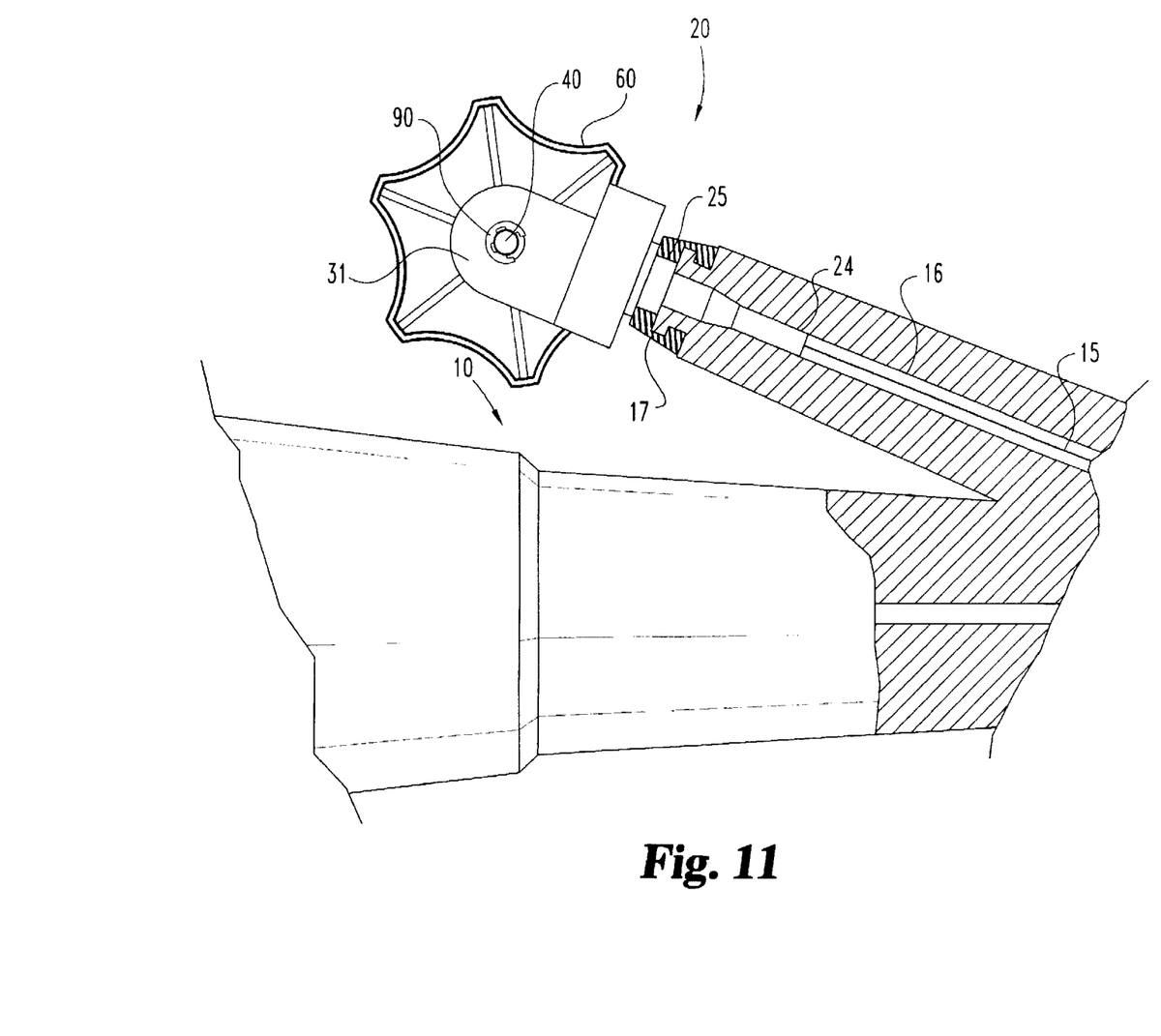
FIG. 11 is a view of the activating mechanism of FIG. 2 after insertion into the operating channel of the endoscope of FIG. 1.

FIG. 3A is a view of mounting component 21. Mounting component includes coupling portion 23, friction-fit portion 24, and outer sealing portion 25. Coupling portion 23 is adapted to fixedly attach to activating component 22. Upon insertion into operating channel 16 through proximal opening 18, friction-fit portion 24 is sized to form a friction fit within operating channel 16. Where endoscope 10 is provided with a sealing member 17 (as shown in FIGS. 10 and 11), outer sealing portion 25 is adapted to seat in and seal with sealing member 17.

Figure 3B:
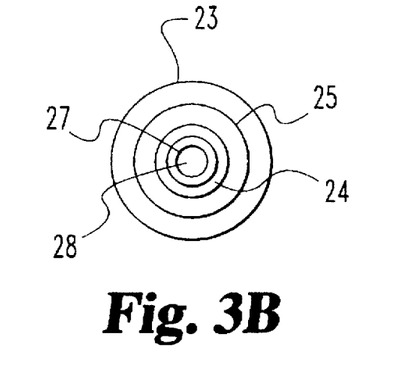
Figure 3C:
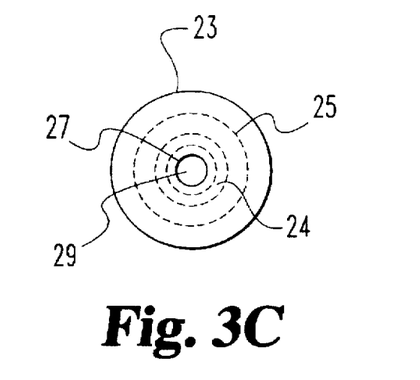

Mounting component 21 also provides first threading channel 27 which extends through mounting component 21. First opening 28 of first threading channel 27 is shown in FIG. 3B and second opening 29 of first threading channel 27 is shown in FIG. 3C. After mounting component 21 has been inserted into operating channel 16, activation line 15 can be threaded into first opening 28 and out of second opening 29 for connection to activating component 22.

Figure 4A:
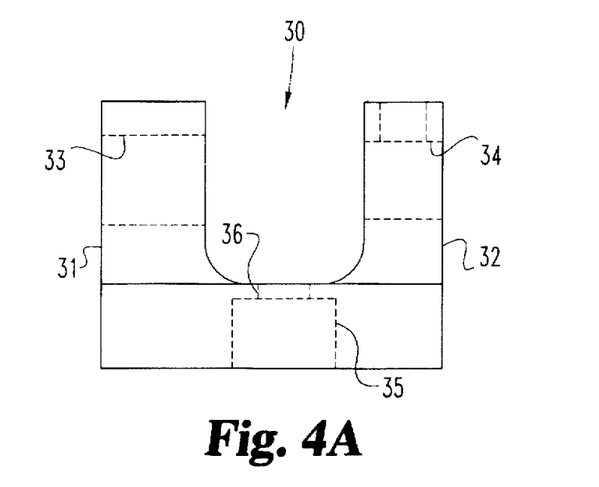
FIGS. 4A-4E are views of a base of the activating mechanism of FIG. 2.
Figure 4B:
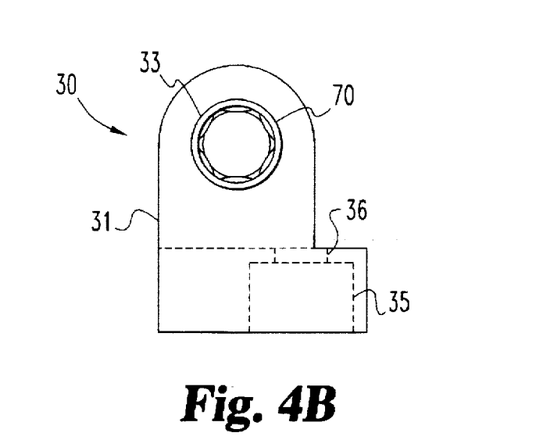
Figure 4C:
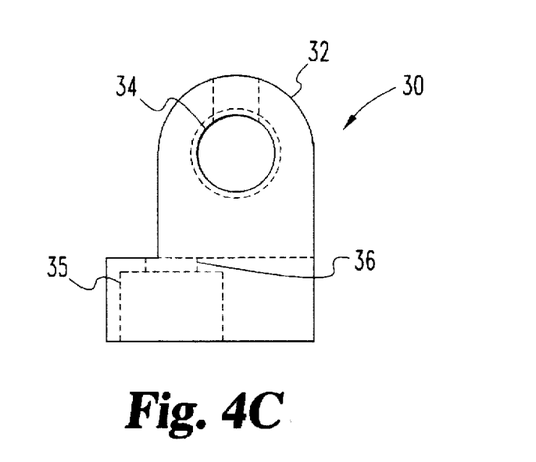
Figure 4D:
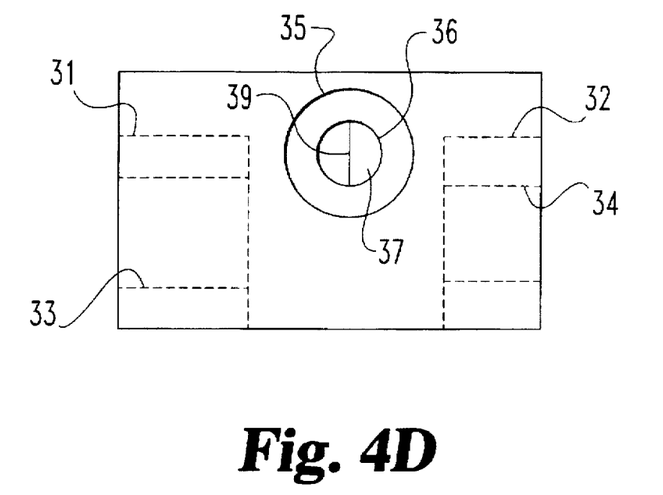
Figure 4E:
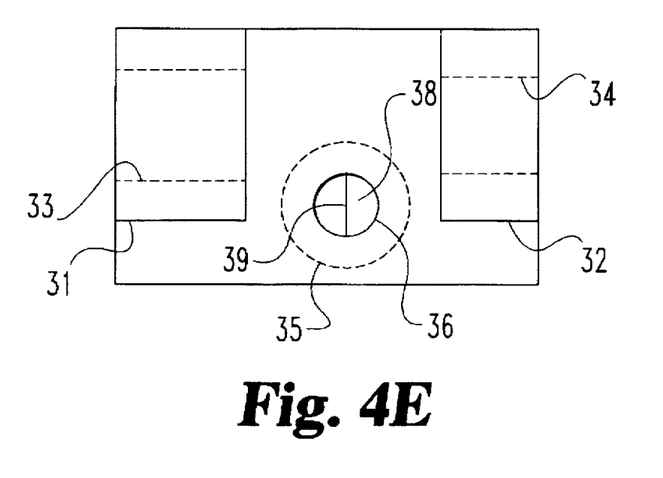

FIG. 4A is a frontal view of base 30. Base 30 includes first arm 31 and second arm 32. As shown in FIG. 4B, first arm 31 provides first receiving opening 33 and as shown in FIG. 4C, second arm 32 provides second receiving opening 34. Base 30 further includes recess 35 located on bottom side portion of base 30 and second threading channel 36 which extends through recess 35 to the top side of base 30. FIG. 4D is a view of the bottom side of base 30, and further shows recess 35 and first opening 37 of second threading channel 36. FIG. 4E is a view of the top side of base 30, showing the top side of first arm 31 and second arm 32, and second opening 38 of second threading channel 36 with inner sealing member 39 located therein. When activation line 15 is threaded through mounting component 21, it is further threaded into first opening 37, through inner sealing member 39, and out of second opening 38 of base portion 30.

Figure 5A:
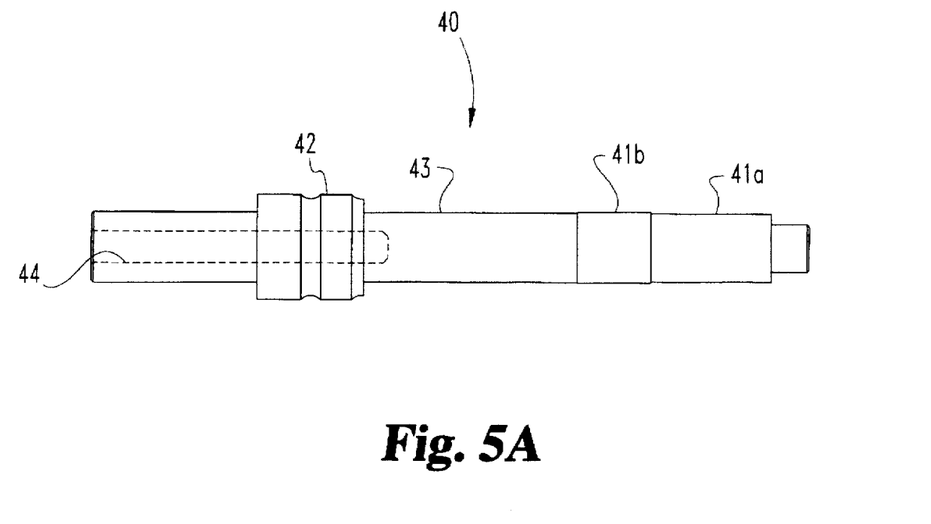
FIGS. 5A-5C are views of a drive pin of the activating mechanism of FIG. 2.
Figure 5B:
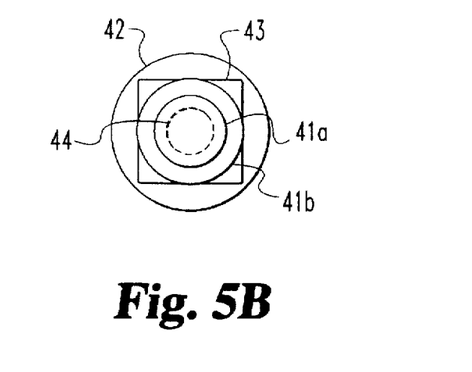
Figure 5C:
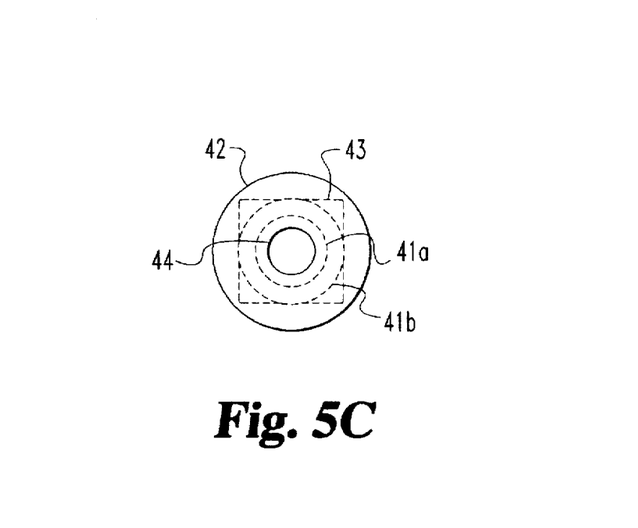

FIG. 5A is a side view of drive pin 40. Drive pin 40 includes first rotating portions 41a and 41b, second rotating portion 42, and third rotating portion 43. Depending upon the mode of operation, rotating portion 41a or rotating portion 41b may be disposed within roller clutch 70 (see FIG. 4b) located within first receiving opening 33 of first arm 31. First rotating portion 41a is dimensioned to rotate within roller clutch 70 within first receiving opening 33 of first arm 31. First rotating portion 41b is dimensioned to engage roller clutch 70 within first receiving opening 33 of first arm 31 to thereby allow for rotation in only one direction when activating component is set in its engaged working mode. FIG. 5B is a front view of drive pin 40. First rotating portion 41a attaches to retaining clip 90 located on the end of first rotating portion 41a. Retaining clip 90 prevents the dislodging of first rotating portion 41a from first receiving opening 33. FIG. 5C is a back view of drive pin 40.

Referring back to FIG. 5A, second rotating portion 42 is disposed within second receiving opening 34 of second arm 32. Second rotating portion 42 is designed to rotate in and slide within second receiving opening 34. Drive pin 40 further includes a threaded hole 44 in second rotating portion 42. Threaded hole 44 is connected to knob 60 by bolt 80. Third rotating portion 43 is designed to be disposed within spool 50.

Figure 6A:
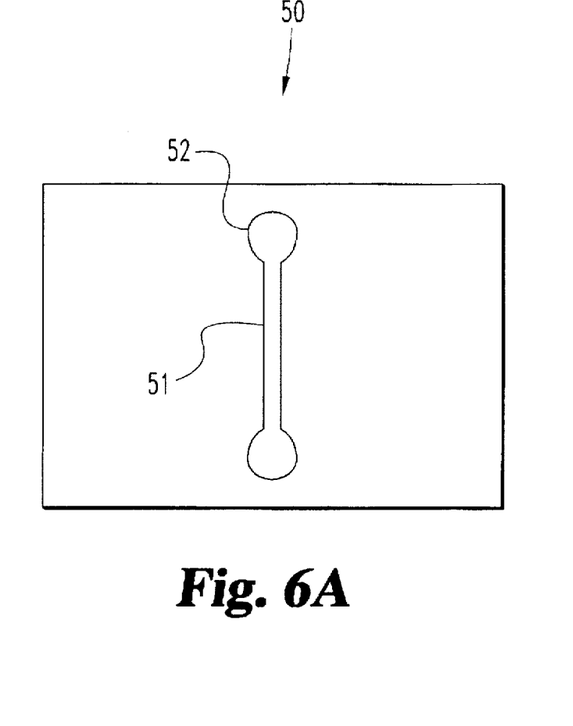
FIGS. 6A-6B are views of a spool of the activating mechanism of FIG. 2.
Figure 6B:
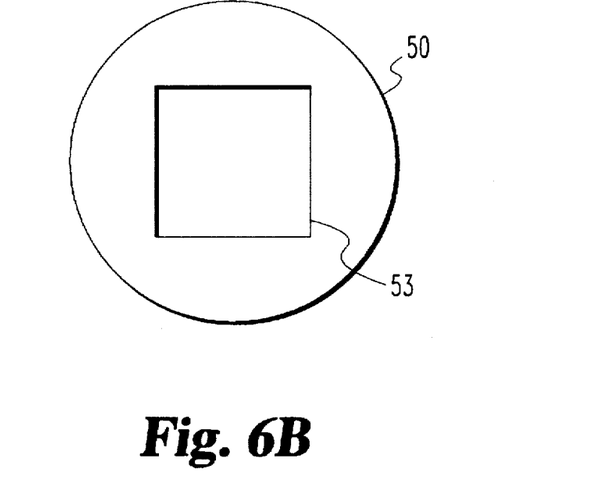

FIG. 6A is a side view of spool 50. Hole 52 and slot 51 receive activation line 15 from second opening 38 of base 30. Activation line 15 is coupled to hole 52 and slot 51 by sliping activation line into slot 51 and placing a knot in activation line 15 into hole 52. FIG. 6B is a front view of spool 50. Spool 50 further includes drive channel 53. Drive channel 53 receives third rotating portion 43 of drive pin 40 both of which have a square crossectional shape. Spool 50 thus rotates in file same direction as drive pin 40 when the drive pin 40 is rotated by knob 60, owing to the engagement between third rotating portion 43 of drive pin 40 and drive channel 53 of spool 50.

Figure 7:
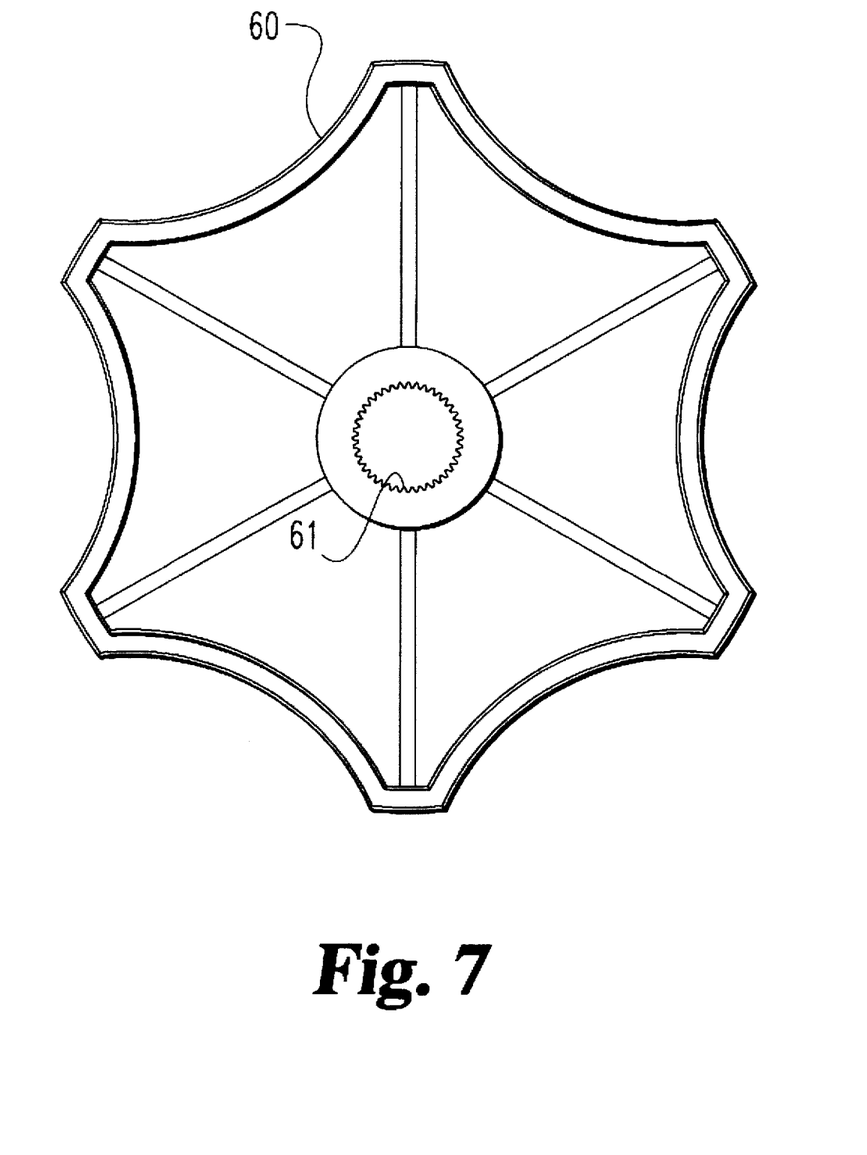
FIG. 7 is a view of a knob of the activating mechanism of FIG. 2.

FIG. 7 is a view of knob 60. Knob 60 includes connecting recess 61. Connecting recess 61 connects with threaded hole 44 of drive pin 40 by means of bolt 80. This connection enables knob 60 to rotate drive pin 40. The connection also prevents second rotating portion 42 of drive pin 40 from dislodging out of second receiving opening 34.

Figure 8A:
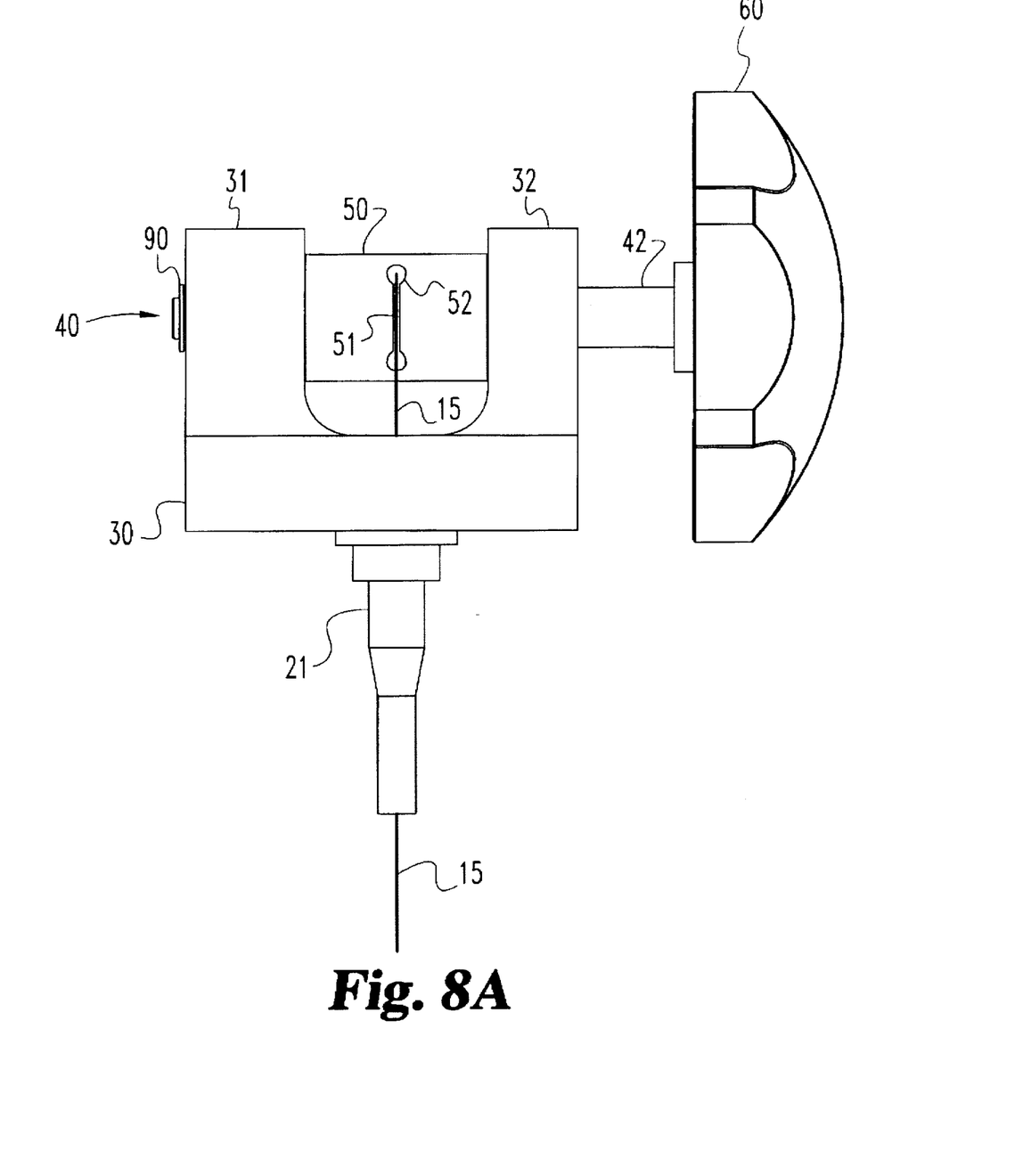
FIG. 8A-8B are views of a disengaged mode of operation of the activating mechanism of FIG. 2 wherein knob 60 is free to rotate in either direction (A or B).
Figure 8B:
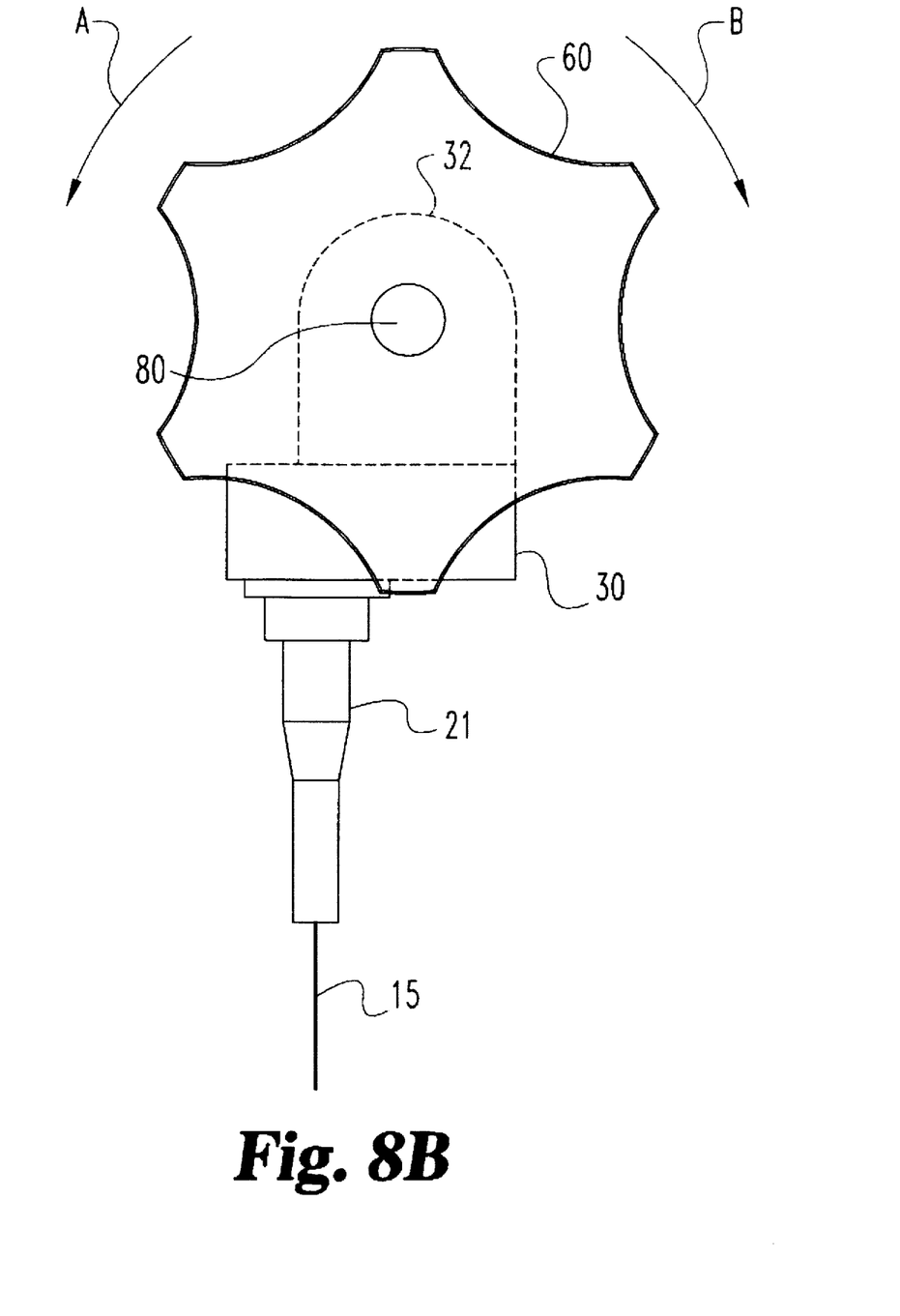
Figure 9A:
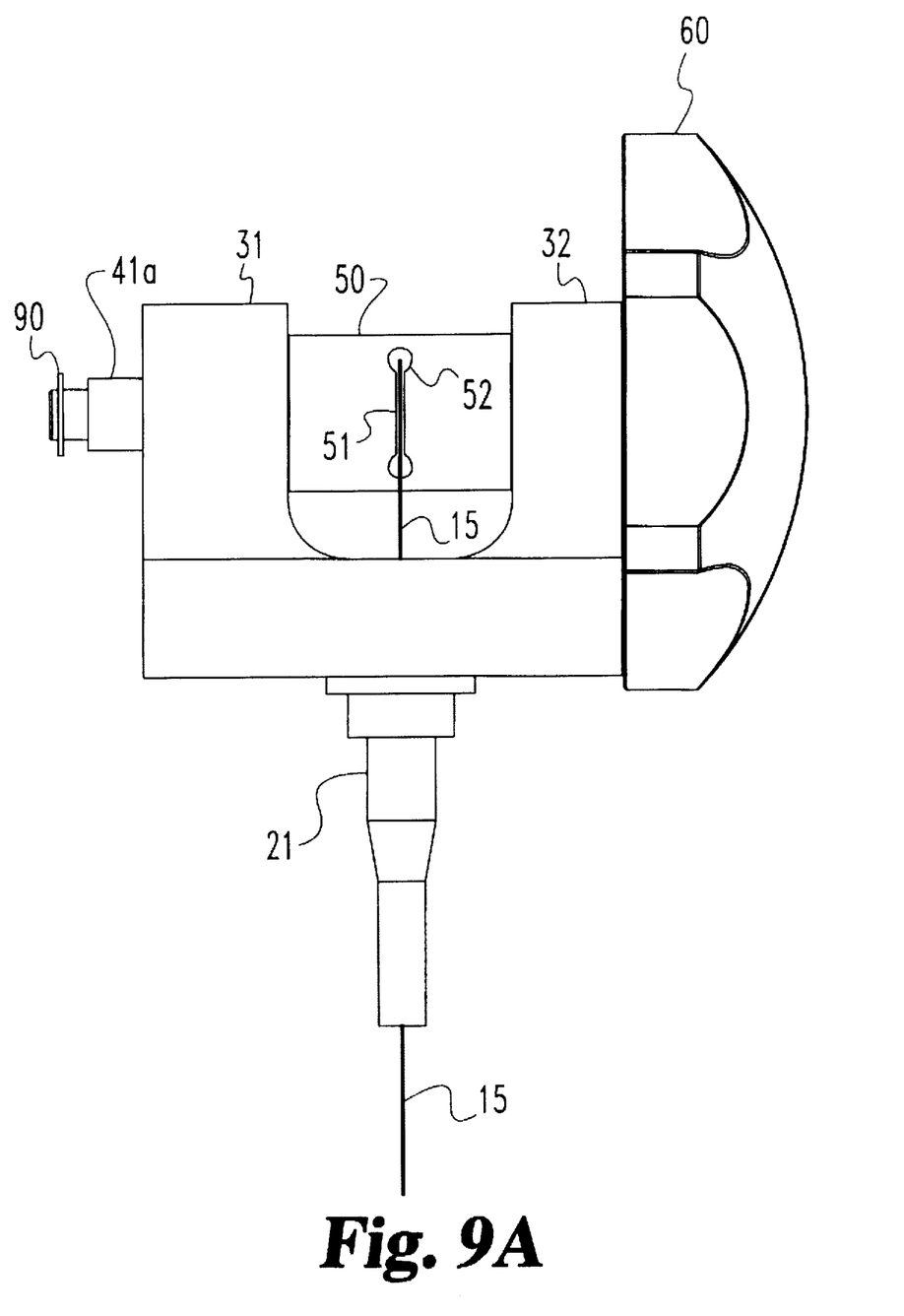
FIG. 9A-9B are views of a working mode of operation of the activating mechanism of FIG. 2 wherein knob 60 is only free to rotate in a single direction.
Figure 9B:
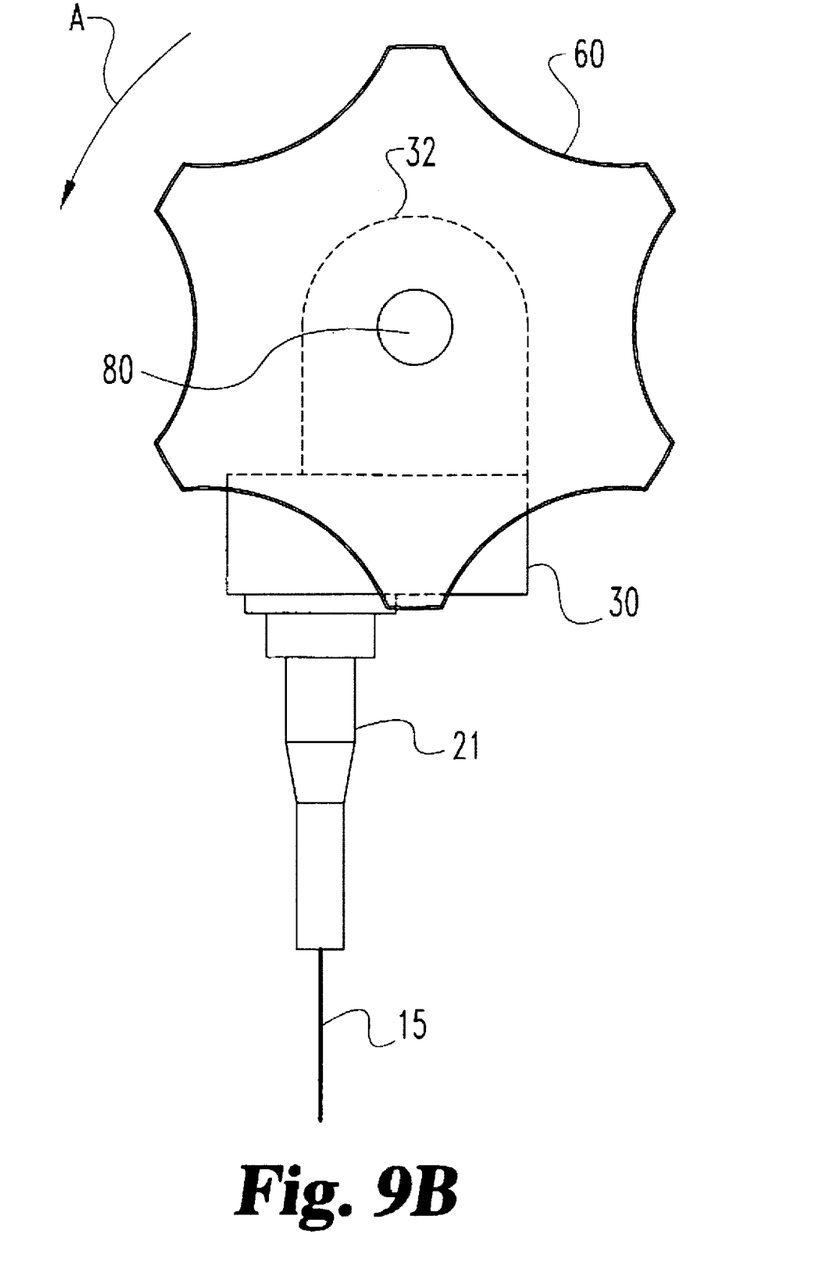

FIGS. 8 and 9 are views of file two modes of operation for activating mechanism 20. FIG. 8A depicts the disengaged mode of operation. Activation line 15 is threaded through mounting component 21 and base 30, and is coupled to spool 50. The disengaged mode of operation is based on a disengaged position of drive pin 40 within roller clutch 70. FIG. 8A discloses second rotating portion 42 of drive pin 40 being substantially disposed outside of second arm 32. FIG. 8A further shows first rotating portion 41 of drive pin 40 being substantially disposed within first arm 31. This is the disengaged position of drive pin 40. Also shown is retaining clip 90 attached to first rotating portion 41. As shown in FIG. 8B, when drive pin 40 is the disengaged position, knob 60 can be rotated freely in either direction (A or B). Alter the attachment of activation line 15 to spool 50, knob 60 can be totaled in either direction to wrap activation line 15 around spool 50. To unwrap activation line 15, knob 60 can be rotated in the opposite direction of the first rotation.

FIG. 9A depicts the working mode of operation. The working made of operation is also based on a working position of drive pin 40 within roller clutch 70. FIG. 9A discloses the second rotating portion segment 42 being substantially disposed within of second arm 32. FIG. 9A further shows rotating portion 41a being substantially disposed outside of first arm 31 with rotating portion 41b in engaging contact with roller clutch 70. As shown in FIG. 9B, when drive pin 40 is in the engaged position, knob 60 can only be rotated in one direction. After the attachment of activation line 15 to spool 50, knob 60 can be rotated in one direction to wrap activation line 15 around the spool 50 under controlled tension to release ligating bands from ligator 14 as desired. Upon completion of the procedure, activating mechanism 20 may be reset in the disengaged mode to release the tension from activation line 15 and allow activation line 15 to be unwound from spool 50 and disconnected therefrom.

FIGS. 10 and 11 show how activating mechanism 20 is mounted to endoscope 10 by inserting mounting element 21 into operating channel 16. For this illustration, endoscope 10 is shown provided with sealing member 17 which is coupled to proximal opening 18 of endoscope 10. FIG. 10 shows the alignment of activating mechanism 20 with proximal opening 18 prior to insertion of mounting element 21 therein. FIG. 11 shows mounting element 21 inserted into operating channel 16. Upon insertion, friction-fitting portion 24 friction fits with receiving portion 19 of operating channel 16, and sealing portion 25 seals with sealing member 17 of endoscope 10. And as described earlier, activation line 15 is threaded into and attached to activating mechanism 20.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An activating mechanism for activating an endoscopic ligator to ligate lesions within a hollow body organ, the endoscopic ligator being positioned at the distal insertion end of an endoscope, the endoscope having an operating channel which extends through the endoscope from an opening at the distal end to an opening at a proximal end of the endoscope, the ligator having an activation line which is threaded through the operating channel of the endoscope to the proximal opening of the endoscope, said activating mechanism comprising:

(a) a mounting component, said mounting component having a first portion dimensioned to be inserted into the operating channel of the endoscope and friction fitted therein, said mounting component including a threading channel extending therethrough for threading the activation line through said mounting component when said first portion of said mounting component is inserted into the operating channel of the endoscope; and (b) an activating component connected to said mounting component, said activating component including
means for attachment of the activation line when the activation line is threaded through said threading channel of said mounting component, and
means for retracting the activation line when the activation line is attached to said activating component whereby the ligating device can be selectively activated.

2. The activating mechanism of claim 1 in which the endoscope further includes a sealing member disposed over the proximal opening of the endoscope, the sealing member having an opening in communication with the proximal opening of the endoscope,
wherein said mounting component further includes a second portion adjacent said first portion, said second portion dimensioned to be received within the sealing member opening when said first portion extends through the operating channel.

3. The activating mechanism of claim 2 wherein said second portion of said mounting component is dimensioned to form a friction fit with the sealing member opening.

4. The activating mechanism of claim 1, wherein said attachment means includes a spool with means for engaging the proximal end of the activation line when the activation line is threaded through said threading channel of said mounting component;
wherein said retracting means includes a knob operationally connected to said spool for manual rotation of said spool, and a base configured to rotationally support said spool, said base defining an opening therethrough; and
wherein said mounting component further includes a coupling portion sized to be received within said opening in said base to connect said activating component to said mounting component.

5. The activating mechanism of claim 1,
wherein said attachment means includes a spool with means for engaging the proximal end of the activation line when the activation line is threaded through said threading channel of said mounting component; and
wherein said retracting means includes a knob operationally connected to said spool for manual rotation of said spool, a base configured to rotationally support said spool, and a one-way clutch engaging said spool to prevent rotation of said spool in one direction and permit rotation of said spool in an opposite direction.

6. The activating mechanism of claim 5, wherein said retracting means further includes a drive pin supported on said base to rotate and reciprocate relative to said base, said drive pin having
a first portion disposed within said spool, said first portion of said drive pin having means for imparting rotational movement from said drive pin to said spool,
a second portion connected to said knob,
a third portion configured to engage said clutch when said drive pin is in a first position, said first position being said third portion disposed within said clutch, and
a fourth portion adjacent said third portion, said fourth portion configured for free-wheel rotation within said clutch when said drive pin is reciprocated to a second position, said second position being said fourth position disposed within said clutch.

7. An activating mechanism for activating an endoscopic ligator to ligate lesions within a hollow body organ, the endoscopic ligator being positioned at the distal insertion end of an endoscope, the endoscope having a channel which extends through the endoscope from an opening at the distal end to an opening at a proximal end of the endoscope, the ligator having an activation line which is threaded through the channel of the endoscope to the proximal opening of the endoscope, said activating mechanism comprising:

(a) a mounting component, said mounting component having a first portion sized to be inserted into the proximal opening of the channel of the endoscope, said mounting component including a threading channel extending therethrough for threading the activation line through said mounting component when said first portion is inserted into the proximal opening of the channel of the endoscope; and (b) an activating component connected to said mounting component, said activating component including
a spool having means for engaging the proximal end of the activation line when the activation line is threaded through said threading channel of said mounting component, and
means for retracting the activation line when the activation line is engaged with said spool, said retracting means preventing rotation of said spool in one direction and permitting rotation of said spool in an opposite direction whereby the ligating device can be selectively activated.

8. The activating mechanism of claim 7 wherein said first portion of said mounting component is sized to form a friction fit within the channel of the endoscope.

9. The activating mechanism of claim 7 in which the endoscope further includes a sealing member disposed over the proximal opening of the channel, the sealing member having an opening in communication with the proximal opening of the endoscope, wherein:
said mounting component includes a second portion adjacent said first portion, said second portion sized to be received within the sealing member opening when said first portion extends through the proximal opening of the channel.

10. The activating mechanism of claim 9 wherein said second portion of said mounting component is sized to form a friction fit with the sealing member opening.

11. The activating mechanism of claim 7, wherein said retracting means includes a knob operationally connected to said spool for manual rotation of said spool, and a base configured to rotationally support said spool, said base defining an opening therethrough; and wherein said mounting component includes a coupling portion sized to be received within said opening in said base to connect said activating component to said mounting component.

12. The activating mechanism of claim 7, wherein said retracting means includes a knob operationally connected to said spool for manual rotation of said spool, a base configured to rotationally support said spool, and a one-way clutch engaging said spool to prevent rotation of said spool in one direction and permit rotation of said spool in an opposite direction.

13. The activating mechanism of claim 12, wherein said retracting means further includes a drive pin supported on said base to rotate and reciprocate relative to said base, said drive pin having     a first portion disposed within said spool, said first portion of said drive pin having means for imparting rotational movement from said drive pin to said spool,     a second portion connected to said knob,     a third portion configured to engage said clutch when said drive pin is in a first position, said first position being said third portion disposed within said clutch, and     a fourth portion adjacent said third portion, said fourth portion configured for free-wheel rotation within said clutch when said drive pin is reciprocated to a second position, said second position being said fourth position disposed within said clutch.

\* \* \* \* \*